United States Patent [19]

Barth

[11] 3,932,604

[45] Jan. 13, 1976

[54] HUMECTANT SWEETENER

[75] Inventor: Jordan B. Barth, East Brunswick, N.J.

[73] Assignee: Colgate-Palmolive Company, New York, N.Y.

[22] Filed: Mar. 11, 1974

[21] Appl. No.: 449,620

Related U.S. Application Data

[63] Continuation-in-part of Ser. No. 317,696, Dec. 22, 1972, abandoned.

[52] U.S. Cl. ................................................. 424/49
[51] Int. Cl.² ........................................... A61K 7/16
[58] Field of Search ................................ 424/49–58

[56] References Cited
UNITED STATES PATENTS

| | | | |
|---|---|---|---|
| 1,484,415 | 2/1924 | Shepherd | 424/51 |
| 3,296,079 | 1/1967 | Griffin | 424/49 |

FOREIGN PATENTS OR APPLICATIONS

| | | | |
|---|---|---|---|
| 2,040,999 | 3/1971 | Germany | 424/180 |
| 7,038,718 | 12/1970 | Japan | |

OTHER PUBLICATIONS

Makinen et al. J. Dent. Res. 51(2) Pt. 1:403–408 (1972) "Enzyme Dynamics of a Cariogenic. Streptococcos. Effect of Xylitol and Sorbitol".
Scheninin et al. Acta Odontol. Scand. 30(2):235–257 (1972) "Effects of Sugars and Sugar Mixtures on Dental Plaque".
Makinen et al. Acta Odontol. Scand. 30(2):259–275 (1972) "Effect of Various Sugars and Sugar Mixtures on the Activity and Formation of Enzymes of Dental Plaque and Oral Fluid".
Grunberg et al. Int. J. Vitam. Nutr. Res. 43(2):227–232 (1973) "Xylitol and Dental Caries. Efficacy of Xylitol in Reducing Dental Caries in Rats".
Muehleman et al. Helv. Odontol. Acta 14(1):48–50 (1970) "Effect on Rat Fissure Caries of Xylitol and Sorbitol".

*Primary Examiner*—Shep K. Rose
*Attorney, Agent, or Firm*—Steven J. Baron; Murray M. Grill; Herbert S. Sylvester

[57] ABSTRACT

A dentifrice which contains a non-cariongenic humectant sweetener. The dentifrice contains non-cariogenic xylitol which has the sweetening strength of sucrose and which also serves as a humectant.

8 Claims, No Drawings

HUMECTANT SWEETENER

This is a continuation-in-part of my copending application, Ser. No. 317,696, filed on Dec. 22, 1972 now abandoned, the benefit of which filing date is claimed.

BACKGROUND OF THE INVENTION

This invention relates to an improved dentifrice. In particular it relates to a dentifrice containing a non-cariogenic sweetener which also acts as a humectant and in some instances as the sole humectant and sweetening component.

The various sweeteners that have been used in dentifrice must be used with a humectant to give a satisfactory product. Xylitol, a pentitol, has the sweetening strength of sucrose, is non-cariogenic, and has humectant properties sufficient to prevent orifice plugging of an uncapped tube of toothpaste.

The importance of the non-cariogenic property in a dentifrice sweetener is obvious. The combination of sweetening and humectant properties in a single compound improves the product and simplifies formulation by making it possible to reduce or even eliminate the content of the standard dentifrice humectants.

SUMMARY OF THE INVENTION

It is an object of this invention to provide a non-cariogenic dentifrice sweetener which also acts as a humectant.

It is another object of this invention to provide a non-cariogenic dentifrice sweetener which may be used in place of part or all of the standard dentifrice humectants and in certain instances, as a full replacement for all the sweetening agents.

It is still another object of this invention to provide a non-cariogenic dentifrice for use in oral hygiene. Other objects will be apparent from a consideration of the specification which follows.

The essential ingredients of my improved dentifrice are an abrasive, water, detergent, and xylitol. If desired, the dentifrice may also contain additional ingredients, such as gums, fluorine containing compounds, flavors, etc.

Suitable abrasives include, for example, dicalcium phosphate, tricalcium phosphate, insoluble sodium metaphosphate, aluminum hydroxide, magnesium carbonate, calcium carbonate, calcium pyrophosphate, calcium sulfate, silica, sodium aluminum silicate, polymethacrylate, bentonite, etc., or mixtures of these materials.

The detergent may be an organic anionic, nonionic, ampholytic or cationic surface-active agent, preferably one which imparts detersive and foaming properties.

Suitable detergents are water-soluble salts of higher fatty acid monosulfates, such as the sodium salts of the mono-sulfated monoglyceride of hydrogenated coconut oil fatty acids, higher alkyl sulfates, such as sodium dodecyl benzene sulfonate, higher alkyl sulfoacetates, higher fatty acid esters of 1, 2 dihydroxy propane sulfonates, and the substantially saturated higher aliphatic acyl amides of lower aliphatic amine carboxylic acid compounds, such as those having 12 to 16 carbon atoms in the fatty acid, alkyl or acyl radicals, and the like. Examples of the last-mentioned amides are N-lauroyl sarcosine, and the sodium, potassium and ethanolamine salts of N-lauroyl, N-myristoyl or N-palmitoyl sarcosinates, all substantially free of soap or similar higher fatty acid material.

Other suitable detergents include nonionic agents, such as condensates or sorbitan monostearate with approximately 60 moles of ethylene oxide, condensates of propylene glycol ("Pluronics") and cationic surface-active germicides and antibacterial compounds such as di-isobutylphenoxyethoxyethyl ammonium chloride, tertiary amines having one fatty alkyl group of from 12 to 18 carbon atoms and two (poly) oxyethylene groups attached to the nitrogen (typically containing a total of from about two to fifty ethenoxy groups per molecule) and salts thereof with acids, and compounds of the structure:

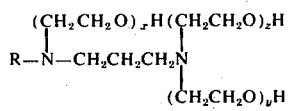

where R is a fatty alkyl group containing from about 12 to 18 carbon atoms, and $x$, $y$ and $z$ total 3 or higher, as well as salts thereof with mineral or organic acids.

Suitable gums or gelling agents include the natural and synthetic gums and gumlike materials, such as Irish moss, gum tragacanth, sodium carboxymethyl cellulose (CMC), polyvinylpyrrolidone, starch, and inorganic thickeners such as "Cabosil" fumed silicon dioxide, "Laponite" (hydrous magnesium silicate clay), Syloid 244 (aerogel silica), and other organic and inorganic materials.

The fluorine-containing compound may be sodium fluoride, stannous fluoride, potassium fluoride, potassium stannous fluoride ($SnF_2$, KF), sodium hexafluorostannate, stannous chlorofluoride, sodium fluorozirconate, and sodium monofluorophosphate.

The flavoring material may be a flavoring oil, such as oils of spearmint, peppermint, wintergreen, clove, sage, eucalyptus, marjoram, cinnamon and lemon. Where a non-bitter flavor such as orange, sodium methyl salicylate or anise licorise is employed, xylitol may serve as the sole sweetener in addition to being the humectant. Still other materials may be incorporated in the dentifrice for various purposes. Examples of these materials are coloring or whitening agents, preservatives, silicones, chlorophyll compounds, ammoniated materials such as urea, diammoniumphosphate, and mixtures thereof, antibacterial agents, etc.

DESCRIPTION OF THE PREFERRED EMBODIMENTS

A dentifrice containing my novel humectant-sweetener may have a composition within the limits set forth below.

| | |
|---|---|
| Abrasive | 10–75% |
| Water | 10–40% |
| Humectant, e.g., glycerine, sorbitol | 0–50% |
| Detergent | 0.5–5% |
| Flavor | 0.1–5% |
| Fluoride ion | 0.05–2% |
| Sweetening agents | 0–2% |
| Binding agents (gums and inorganic gelling agents) | up to 10% |
| Xylitol | 5–60% |

The preferred xylitol content of the dentifrice is from about 10% to about 25% To avoid a bitter taste (or aftertaste) the amount of water present should be no more than that required to give at least a 10 or 15% solution of xylitol. The amount of standard humectant used will depend on the xylitol content. If a dentifrice contains at least about 15–20% xylitol it is not necessary to use an additional humectant because orifice plugging will not occur when the toothpaste tube is left uncapped overnight. Preferably about 0.2% of a standard sweetening agent will be used. The exact amount of this ingredient will depend mainly on the taste desired. The amounts of the other ingredients may be varied as desired.

The following specific examples are further illustrative of the nature of the present invention but it is to be understood that the invention is not limited thereto. The amounts and proportions in the examples are by weight unless otherwise indicated.

| Example I | |
|---|---|
| Xylitol | 5.00% |
| Carboxymethyl cellulose | 1.10 |
| Glycerine | 9.99 |
| Sorbitol | 11.90 |
| Sodium benzoate | 0.50 |
| Water | 24.00 |
| Na₂PO₃F | 0.76 |
| TiO₂ | 0.40 |
| Insoluble sodium metaphosphate | 36.85 |
| Hydrated alumina | 5.00 |
| Anhydrous dicalcium phosphate | 1.00 |
| Sodium lauryl sarcosinate | 2.00 |
| Flavor | 1.50 |
| TOTAL | 100.00% |

When the teeth are brushed with this dental cream a pleasant taste develops and remains in the oral cavity during brushing and for a short time thereafter.

| Example II | |
|---|---|
| Xylitol | 10.00% |
| Carboxymethyl cellulose | 0.90 |
| Glycerine | 9.99 |
| Sorbitol | 7.00 |
| Sodium benzoate | 0.50 |
| Water | 19.60 |
| Na₂PO₃F | 0.76 |
| TiO₂ | 0.40 |
| Insoluble sodium metaphosphate | 41.85 |
| Hydrated alumina | 1.00 |
| Anhydrous dicalcium phosphate | 5.00 |
| Sodium lauryl sarcosinate | 2.00 |
| Flavor | 1.00 |
| TOTAL | 100.00% |

When the teeth are brushed with this composition, the results are generally the same as those obtained with the composition of Example I.

| Example III | |
|---|---|
| Xylitol | 10.00% |
| Carboxymethyl cellulose | 1.10 |
| Glycerine | 22.00 |
| Sodium benzoate | 0.50 |
| Water | 24.59 |
| Na₂PO₃F | 0.76 |
| CaCO₃ | 37.25 |
| Hydrated alumina | 1.00 |
| Sodium lauryl sulfate | 1.50 |
| Flavor | 1.30 |
| TOTAL | 100.00% |

Despite certain differences in the ingredients when the teeth are brushed with this composition the results are generally the same as those obtained with the compositions of Examples I and II.

| Example IV | |
|---|---|
| Xylitol | 25.00% |
| Carboxymethyl cellulose | 0.90 |
| Glycerine | 1.71 |
| Sodium benzoate | 0.50 |
| Water | 19.88 |
| Na₂PO₃F | 0.76 |
| TiO₂ | 0.40 |
| Insoluble sodium metaphosphate | 41.85 |
| Hydrated alumina | 1.00 |
| Anhydrous dicalcium phosphate | 5.00 |
| Sodium lauryl sarcosinate | 2.00 |
| Flavor | 1.00 |
| TOTAL | 100.00% |

When the teeth are brushed with this composition, the results are generally the same as those obtained when the compositions of the previous examples are used. In addition, no orifice plugging occurs when the tube is left uncapped overnight.

| Example V | |
|---|---|
| Xylitol | 50.00% |
| Carboxymethyl cellulose | 1.00 |
| Sodium benzoate | 0.50 |
| Water | 20.50 |
| Sodium aluminum silicate | 25.00 |
| Sodium lauryl sulfate | 2.00 |
| Flavor | 1.00 |
| TOTAL | 100.00% |

Again, despite the differences in the ingredients the results obtained when this composition is used are generally the same as those obtained with the compositions of the previous examples.

It will be apparent to those skilled in the art that various modifications may be made to the specific compositions described and equivalents substituted therefor.

What is claimed is:

1. A dental cream requiring a humectant, said humectant consisting essentially of at least about 15% by weight of xylitol, effective, as sole humectant, to prevent orifice plugging when said cream is left uncapped overnight.

2. The composition claimed in claim 1 wherein the xylitol content is from about 15 to about 60% by weight.

3. The composition claimed in claim 1 wherein the xylitol content is from about 15 to about 25% by weight.

4. The composition claimed in claim 1 wherein there is present abrasive material and detergent.

5. The composition claimed in claim 2 wherein there is present abrasive material and detergent.

6. The composition claimed in claim 3 wherein there is present an additional sweetening agent and a flavor material.

7. The composition claimed in claim 1 wherein said xylitol is the sole sweetening agent.

8. The composition claimed in claim 7 additionally containing a non-bitter flavor.

* * * * *